United States Patent [19]
Jenkins

[11] Patent Number: 5,542,845
[45] Date of Patent: Aug. 6, 1996

[54] DENTAL SYRINGE SAFETY SHEATH WITH MODIFIED DUCKBILL VALVE

[75] Inventor: Thomas E. Jenkins, Riverside, Calif.

[73] Assignee: A.C. Hoffman Engineering, Inc., Riverside, Calif.

[21] Appl. No.: 289,303

[22] Filed: Aug. 11, 1994

[51] Int. Cl.⁶ ........................................... A61C 1/16
[52] U.S. Cl. ............................................... 433/116
[58] Field of Search ...................... 433/116, 80; 137/846, 137/847, 849

[56] References Cited

U.S. PATENT DOCUMENTS

| | | | |
|---|---|---|---|
| 2,644,663 | 7/1953 | Klinger | 137/846 |
| 3,066,767 | 12/1962 | Djordjevitch | 137/847 |
| 3,896,849 | 7/1975 | Ervin et al. | 137/847 |
| 3,941,149 | 3/1976 | Mittleman | 137/846 X |
| 4,434,810 | 3/1984 | Atkinson | 137/846 X |
| 4,524,805 | 6/1985 | Hoffman . | |
| 4,859,182 | 8/1989 | Nerli . | |
| 4,998,880 | 3/1991 | Nerli . | |
| 5,197,875 | 3/1993 | Nerli . | |

Primary Examiner—Nicholas D. Lucchesi
Attorney, Agent, or Firm—Poms, Smith, Lande & Rose

[57] ABSTRACT

A dental syringe safety sheath having a modified duckbill valve for minimizing cross-contamination between dental patients is provided. The sheath includes a generally tubular body member having a nozzle engaging portion and a discharge portion. The nozzle engaging portion is configured to substantially fit over and cover the nozzle of a dental syringe having a discharge orifice. The discharge portion defines a fluid passageway having an inlet adjacent the discharge orifice and outlet downstream therefrom. The fluid passageway progressively narrows in cross-section between the inlet and the outlet to form a substantially wedge-shaped cavity terminating in a slit disposed between a pair of opposing sealing lips. The cross-section of the sealing lips between the ends of the slit is wider than the corresponding cross-section of the sealing lips at the lip margins. As an additional or alternative feature of the present invention, the collective width of the sealing lips measured along a discrete portion of the lips between the ends of the slit being at least as great as the length of the lips measured along the slit.

12 Claims, 1 Drawing Sheet

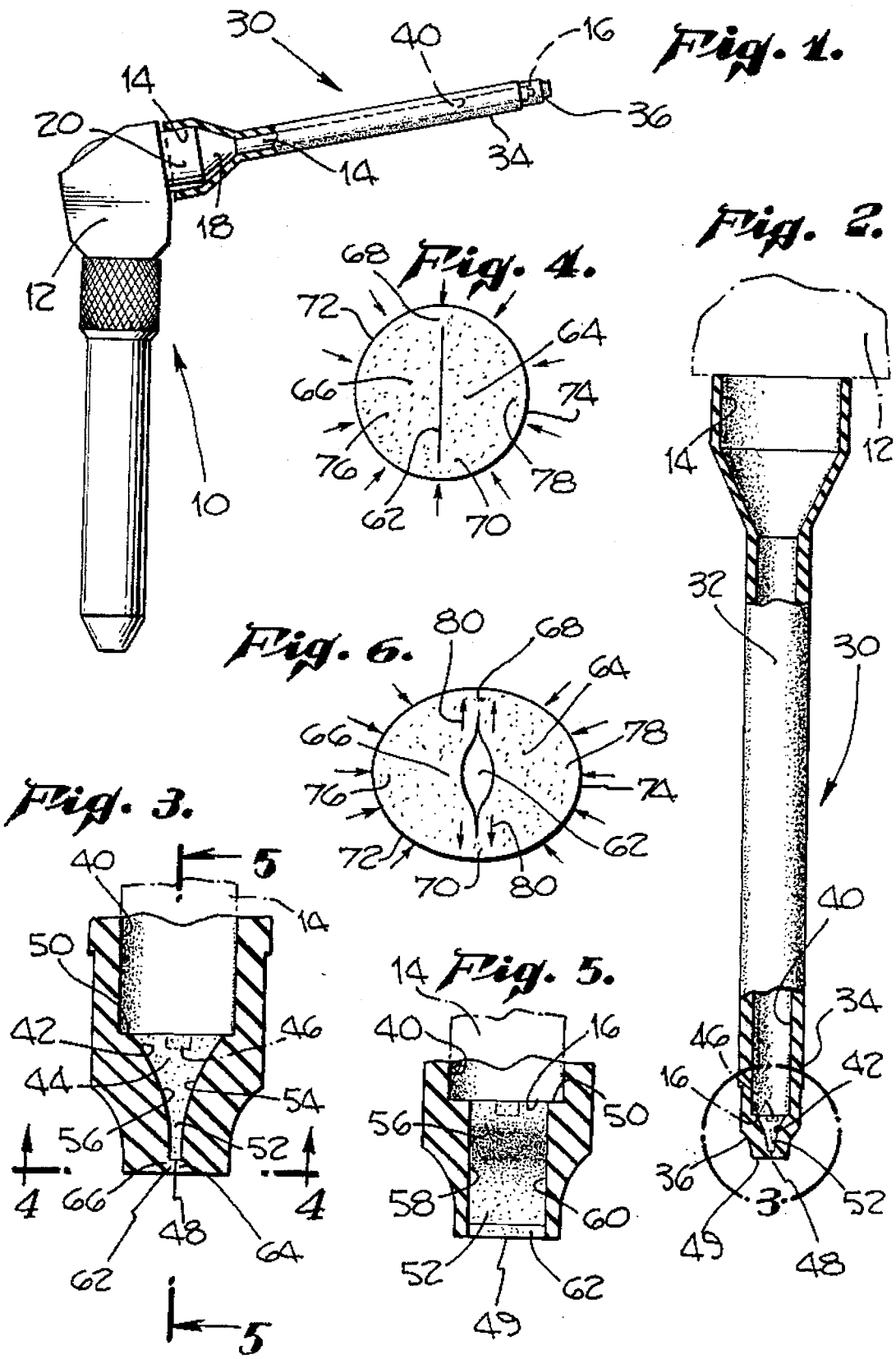

DENTAL SYRINGE SAFETY SHEATH WITH MODIFIED DUCKBILL VALVE

FIELD OF INVENTION

The present invention relates generally to one-way valves of duckbill type construction, and more particularly, to duckbill bill valves utilized in conjunction with dental syringe safety sheath apparatus to minimize residual cross-contamination between patients.

BACKGROUND OF THE INVENTION

Dental syringe apparatus are employed by dentists to deliver a stream of pressurized fluid such as water or air to the inside of a dental patient's mouth. Dental syringes are typically connected to pressurized fluid delivery systems and include a handpiece having a trigger mechanism and an elongate nozzle for generating a pressurized fluid stream.

Most dental syringe systems also include draw-back apparatus which produce a partial vacuum in the dental syringe so as to draw fluid located within the syringe back into the delivery system upon release of the trigger mechanism.

While draw-back apparatus prevent the leaking or dripping of liquid from the discharge orifice of a syringe nozzle when the syringe is not in use, they are not without their disadvantages. More specifically, draw-back apparatus may cause a dental patient's blood, saliva and other residual bodily fluids to be sucked into a syringe, especially if the terminal end of the syringe nozzle is in contact with or in close proximity to a work area within the patient's mouth when the trigger mechanism is released. The drawn-in bodily fluids will remain with the syringe until the trigger mechanism is reactivated. Upon reactivation of the trigger mechanism, the drawn-in fluids will be discharged from the syringe, possibly into another patient's mouth, thus causing the transmission of of any contagious diseases carried in the residual bodily fluids of a previous patient to a subsequent patient.

Accordingly, unless precautions are taken, the use of dental syringe systems to dispense fluid streams to work areas within a dental patient's mouth presents a significant risk of residual cross-contamination to dental patients.

In an effort to reduce the health risks associated with the use of dental syringe systems, a variety of dental syringe safety sheaths have been conceived. These dental syringes safety sheaths typically include a disposable resilient tubular member which is configured to cover the nozzle of a dental syringe and an aperture at the terminal end thereof through which a preferred fluid stream may be discharged. Such safety sheaths also commonly include valve means intended to prevent the residual bodily fluids from be drawn back into the sheaths upon termination of the fluid stream to a work area within a patient's mouth.

One type of valve which has been used to prevent the reverse flow of fluids in a wide variety of applications is the duckbill valve. A typical duckbill valve is shown generally at 50 in FIGS. 6, 7 and 8 of U.S. Pat. No. 4,524,805, issued to the above-identified inventor. Valve 50 includes a body member 52 which defines a fluid passageway 54. Body member 52 smoothly tapers from an inlet end 56 to form a wedge edge shaped outlet end 58 having an outlet slit 59 defining a pair of resilient sealing lips 60 and 62 of a uniform width. The cross-section of sealing lips 60 and 62 between the ends of outlet slit 59 is substantially narrow relative to the length of slit 59.

In operation, valve 50 is usually positioned in line with a fluid conducting conduit (not shown). A stream of pressurized fluid is directed along the conduit and into the inlet end 56 of the valve 50 along the fluid passageway 54 to outlet end 58 where the pressure exerted by the fluid flowing between normally closed sealing lips 60 and 62 deforms the lips so as to permit fluid flow therethrough. If fluid flow stops or reverses direction, the resilient lips are intended to have a closing bias such that the lips will resume their normal shape and position in sealing engagement against one another.

Duckbill valves are usually formed of a resilient elastomeric material which is molded into a configuration substantially similar to that shown in FIGS. 6–8 of the U.S. Pat. No. 4,524,805 referenced above. The forming process often results in a slight amount of heat induced shrinkage to the resilient material comprising the valve member 52. Significantly, the amount of lip shrinkage in lengthwise direction is typically greater than the amount of shrinkage in the tranverse direction. In consequence, a slight opening bias is typically imparted along the length of lips 60 and 62. The slight opening bias normally urges the sealing lips into a slightly open position under no flow conditions. Duckbill valves of conventional duckbill type construction thus are commonly susceptible to small amounts of leakage under no flow and low flow conditions.

While small reverse leaks in a duck flow valve may be acceptable in non-dental applications, it is clear that even the most insubstantial reverse leak in a dental syringe poses an unacceptable health risk to dental patients.

Previous attempts at preventing reverse flow leakage in dental syringe sheath apparatus are exemplified by U.S. Pat. Nos. 4,998,880 and 5,197,875, issued to Nerli. The '880 patent teaches the use of a flap-type valve and/or ball-type valve insert, in conjunction with dental syringe safety sheath apparatus, to minimize residual cross-contamination problems. It is believed that the flap-type valve described in the '880 patent is susceptible to reverse flow leakage problems. While the ball-type valve may be effective in preventing reverse flow, the insert adds to the complexity and expense of the safety sheath. The '875 patent teaches the use of a duckbill valve also to minimize residual cross-contamination between dental patients. However, as noted above, duckbill valves typically have a slight opening bias under no flow conditions and thus, like the flap-type valve of the '880 patent, are susceptible to reverse flow leakage problems. In this regard, it is noted that the patentee of the '875 patent retained the assignee of the present application to manufacture a prototype of a dental syringe safety sheath having a conventional duckbill valve at its terminal end. The prototype, manufactured in accordance with the patentee's specifications, included a pair of sealing lips of a rectangular cross-section (between the ends of the slit disposed therebetween) terminating in a pair of lip margins having rounded outer edges. The sealing lips had a combined width of 1.3 millimeters (between the ends of the slit) as compared to a sealing lip length (measured along the slit) of 3.7 millimeters. Tests of the prototype indicated that the valve did not adequately resist reverse flow leakage problems and that, as such, the design was not suitable for use in dental applications.

A low cost duckbill valve which is more resistant to reverse flow leakage is illustrated in FIGS. 1–5 of U.S. Pat. No. 4,524,805 referenced above. The improved duckbill valve 10 described in that patent includes a pair of sealing lips 20 and 22 having enlarged or widened lip margins 24 and 26 adjacent the opposing ends of slit 19 which elastically resist the opening of the lips 20 and 22. While it is believed that a duckbill valve manufactured in accordance with the disclosure of that patent demonstrates improved resistance to reverse leakage problems relative to predecessor designs, valve 10 was not conceived specifically for use in medical-related applications wherein reverse flow leakage poses significant health risks to dental patients. Thus, there remains a need for one-way valve of duckbill type construction which is even more resistant to reverse flow leakage problems and which can be utilized in conjunction with a dental syringe safety sheath apparatus to minimize the risk of residual cross-contamination between dental patients.

Accordingly, it is a principal object of the present invention to provide a dental syringe safety sheath with a modified duckbill valve having a closing bias which is more resistant to reverse flow leakage.

It is also an object of the present invention to provide a dental syringe safety sheath having a modified duckbill valve which can be easily engaged with or disengaged from the nozzle of a dental syringe and which can be disposed of after use with each dental patient.

It is yet a further object of the present invention to provide such a dental syringe safety sheath at a low cost.

SUMMARY OF THE INVENTION

The present invention accomplishes these and other objects through the provision of a dental syringe safety sheath having duckbill valve modified to resist the the heat induced shrinkage problems typically associated with one-way valves of duckbill type construction.

It is has been discovered the increased heat induced shrinkage in lengthwise direction of the sealing lips of conventional duckbill valves relative to the tranverse direction is the result of the relative thinness of the sealing lips. Test data indicate the rate of heat induced shrinkage in elastomeric materials is directly related to the thickness of the material. The greater the thickness in a specific direction, the greater the shrinkage. As noted above, a standard duckbill valve has sealing lips formed from a material having a rectangular cross-section which is substantially longer (in the direction of the slit) than it is wide. In consequence, there is more shrinkage in the lengthwise direction and thus a slight opening bias is imparted to the sealing lips.

This problem of undesirable heat induced shrinkage can be offset by increasing the thickness of the sealing lips relative to the length of the lips. More particularly, the problems of undesirable heat induced shrinkage can be offset by increasing the thickness of the sealing lips such that the collective width of the sealing lips measured along a discrete portion of the lips between the ends of the slit is at least as great as the length of the lips measured along said slit. The increased thickness of the sealing lips provides for more consistent shrinkage in the lengthwise and tranverse directions thereby minimimizing the tendency of the sealing lips to biased in a slightly open position under no flow conditions.

A dental syringe safety sheath in accordance with the present invention includes a generally tubular body member having a nozzle engaging portion and a discharge portion. The nozzle engaging portion is configured to substantially fit over and cover the nozzle of a dental syringe having a discharge orifice. The discharge portion defines a fluid passageway having an inlet adjacent the discharge orifice of the syringe and outlet downstream therefrom. The fluid passageway progressively narrows in cross-section between the inlet and the outlet to form a substantially wedge-shaped cavity terminating in a slit disposed between a pair of opposing sealing lips having lip margins at the end thereof.

As a feature of the present invention, the cross-section of the sealing lips between the ends of the slit is generally wider that the corresponding cross-section of the sealing lips at the lip margins.

As yet one more additional or alternative feature of the present invention, the collective width of the sealing lips measured along a discrete portion of the lips between the ends of the slit is at least as great as the length of the lips measured along said slit.

In a preferred embodiment, the sealing lips have substantially circular cross-section. This circular configuration ensures consistent, radially directed, heat induced shrinkage of the sealing lips during the forming process and thus overcomes the deficiencies associated with one-way valves of conventional duckbill type construction.

Advantageously, the thickening of resilient material forming the portion of the sealing lips which extends between the ends of the slit also increases the resistance of the normally closed sealing lips to opening upon exertion of a pressurized fluid therebetween and increases the tendency of the sealing lips to move back into sealing engagement upon termination of the fluid stream.

It is submitted that those skilled in the art will obtain a better understanding of the construction and mode of operation of the present invention as well as become aware of the additional advantages and objects thereof from a consideration of the following description of preferred exemplary embodiments taken in combination with the accompanying drawings.

BRIEF DESCRIPTION OF THE DRAWINGS

FIG. 1 is a side view of a dental syringe safety sheath in accordance with the present invention, shown in assembled relation to a conventional dental syringe.

FIG. 2 is a side view of the dental syringe safety sheath of FIG. 1 including a partial section to show the progressive narrowing of the fluid passageway in the discharge portion of the safety sheath.

FIG. 3 is an enlarged view of the partial section of FIG. 2 taken through line 3 in FIG. 2.

FIG. 4 is an enlarged end view of the sealing lips shown in FIG. 3.

FIG. 5 is a partial sectional view of FIG. 3 taken through lines 5—5.

FIG. 6 shows the sealing lips of FIG. 4 forced apart due to pressure exerted by fluid flow therebetween.

DETAILED DESCRIPTION OF PREFERRED EXEMPLARY EMBODIMENT(S)

Referring initially to FIGS. 1 and 2, a preferred exemplary embodiment of a dental syringe safety sheath in accordance with the present invention is shown in assembled relation to a conventional dental syringe which is indicated generally at 10.

The dental syringe 10 includes a hand-piece 12 having a trigger mechanism (not shown) and a generally cylindrical nozzle 14 for generating a pressurized stream of water, air, or a water-air mixture. The nozzle 14 includes a discharge orifice (not shown) at its terminal end 16 and a generally bell-shaped portion 18 at its base end 20. The dental syringe 10 is connected to a pressurized fluid delivery system including draw-back apparatus (not shown).

A disposable dental syringe safety sheath adapted for use with the dental syringe 10 is indicated generally at 30 in FIGS. 1 and 2. The safety sheath 30 is comprised of a generally tubular resilient body member 32 having a nozzle engaging portion 34 and a tapered discharge portion 36 as seen in FIG. 2. The nozzle engaging portion 34 includes inner surface 40 which is configured to engage the outer surface of the terminal end 16 of the nozzle 14 in a close fitting relation. Preferably, the nozzle engaging portion 34 is formed so as to be easily disengageable from nozzle 14. The discharge portion 36 of safety sheath 30 includes an inner surface 42 which defines a fluid passageway 44 having an inlet 46 adjacent the discharge orifice of syringe 10 and an outlet 48 at the terminal end 49 of discharge portion 36.

As best shown in FIGS. 3 and 5, the fluid passageway 44 progressively narrows in cross-section between inlet 46 and outlet 48 to form a substantially wedge edge shaped cavity 52. The wedge shaped cavity is defined in part by convergent arcuate surfaces 54 and 56 and in part by substantially parallel inner walls 58 and 60. The wedge shaped cavity 52 terminates in a slit 62 disposed between a pair of opposing sealing lips 64 and 66 having lip margins 68 and 70 and outer surfaces 72 and 74. In an alternative embodiment, the convergent surfaces 54 and 56 are substantially planar rather than arcuate.

The cross-section of fluid passageway 44 shown in FIGS. 3 and 5 is slightly reduced relative to the cross-section of the cavity defined by inner surface 40 of the nozzle engaging portion 34 so as to define a shoulder 50 which abuts against the terminal end 16 of the nozzle 14 when the sheath 30 is in assembled relation thereto. The shoulder 50 assists the user in properly positioning the safety sheath 30 over nozzle 14 and helps to prevent leakage of fluids between outer surface of the nozzle 14 and the inner surface 42 of nozzle engaging portion 36.

As best shown in FIG. 4, the material forming sealing lips 64 and 66 has a substantially circular cross-section. The lips increase in thickness as the sealing lips extend from the lip margins 68 and 70 to generally central portions 76 and 78 of the sealing lips 64 and 66. The circular configuration of the sealing lips ensures consistent, radially directed, heat induced shrinkage of the sealing lips thus eliminating any tendency of the lips to be biased toward the open position under no flow conditions.

Advantageously, the increased thickness of the resilient material forming sealing lips 64 and 66 also increases the fluid pressure required to separate lips and ensures that the sealing lips have sufficient closing bias to displace any residual fluids which may be located between the sealing lips under low flow or no flow conditions.

It is preferable that the material defining the wedge-shaped cavity 52 also have a substantially circular cross-section, particularly through the plane immediately adjacent the sealing lips 64 and 66, as best shown in FIGS. 3 and 5. This ensures the material defining wedge-shaped cavity 52 also shrinks in a manner which will minimize the likelihood of an opening bias being imparted to the sealing lips adjacent thereto.

In operation, safety sheath 30 functions as a one way valve which prevents blood, saliva and other possibly contaminated bodily fluids from being sucked into sheath 30 when the trigger mechanism of the dental syringe 10 is released and the draw back apparatus is activated. Initially, water, air or a combination of the two, enters fluid passageway 44 through inlet 46, flows through the discharge portion 36 of body member 32, to the outlet 48, where the fluid pressure distorts the flexible elastomeric material of lips 64 and 66 to force lips 64 and 66 apart, opening slit 62. The resiliency of the material forming lips 64 and 66 allows lips 64 and 66 to be separated by the flow of pressurized fluid through fluid passageway 44. However, when the direction of the fluid flow is stopped or reversed, the compressive force exerted by the resilient material forming lips 64 and 66 forces lips 64 and 66 into sealing engagement against one another.

Notably, the compressive forces exerted by the material forming the lip margins 68 and 70 is relatively small as compared to the compressive forces exerted by the thicker material which extends between the ends of slit 62. Accordingly, the pressure exerted by a fluid disposed between sealing lips 64 and 66 tends to urge the lip margins 68 and 70 outwardly as indicated by arrows 80 in FIG. 6. This outward urging of lip margins 68 and 70 increases the tensile forces exerted along the length of lips 64 and 66 thus increasing the closing bias of the sealing lips 64 and 66 when pressurized fluid is disposed between the sealing lips.

It is preferred that safety sheath 30 be of a unitary construction and formed of a resilient elastomeric material having the qualities of natural rubber. This construction is preferred as it simplifies the manufacturing and operation of safety sheath 30 and reduces the associated cost. However, it will be understood by those skilled in the art that the portion of the sheath 30 comprising a one-way valve of duckbill type construction, modified in accordance with the teachings of the present invention, may be formed separately and still remain within the scope and teachings of the present invention.

Those skilled in the art will appreciate a duckbill valve may be configured other than as shown in the drawings as still remain within the scope and teachings of the present invention. For example, while present invention contemplates that the material forming the sealing lips have a substantially circular cross-section, it will be appreciated that the cross-section of the sealing lips could be slightly or even substantially elliptic with the major axis extending perpendicular to the slit. Other configurations are also possible. While any thickening of the material between the ends of the slit is believed to increase the closing bias of the sealing lips and to resist problems associated with heat induced shrinkage, it is desirable that the collective width of the sealing lips measured along a discrete portion of the lips between the ends of the slit be no less than about two thirds as great as the length of the lips measured along said slit. Preferably, however, the collective width of the sealing lips measured along a discrete portion of the lips between the ends of the slit should be at least as great as the length of the lips measured along said slit. This helps to ensure that any shrinkage in the tranverse direction will be at least as great as the shrinkage in the lengthwise direction thereby minimimizing the tendency of the sealing lips to biased in a slightly open position under no flow conditions.

It is therefore seen that a dental syringe safety sheath having a one way valve of duckbill type construction may be modified to provide increased resistance to reverse leaking and resultant residual cross-contamination between dental patients. The sealing lips of a safety sheath configured in accordance with the present invention are truly biased in the closed position under no and low flow conditions and may therefore be used in conjunction with dental syringe systems with or without draw-back apparatus.

Although the present invention has been described in detail with regard to the preferred embodiment and drawings thereof, it should be apparent to those skilled in the art that the within disclosures are exemplary only and various other alternatives, adaptations and modifications may be accomplished but still fall within the scope and spirit of the present invention. In particular, it will be appreciated that a duckbill valve manufactured in accordance with the teachings of the present invention may be used in other applications where it is desirable to prevent leakage under no flow, low flow or reverse flow conditions.

Accordingly, the scope of the present invention is not limited to the specific embodiment as illustrated herein but is limited only by the following claims and equivalents thereof.

What is claimed is:

1. A dental syringe safety sheath adapted for use with a dental syringe having a nozzle, comprising:

a generally tubular resilient body member having a nozzle engaging portion and a tapered discharge portion, said nozzle engaging portion being configured to substantially fit over and cover the nozzle of a dental syringe having a discharge orifice, said tapered discharge portion adapted to extend downstream from said discharge orifice;

said tapered discharge portion defining a tapered external surface and an interior fluid passageway having an inlet adapted to be adjacent said discharge orifice and an outlet downstream therefrom, said fluid passageway progressively narrowing in cross-section between said inlet and said outlet to form a substantially wedge-shaped cavity terminating in a slit disposed between a pair of opposing sealing lips having lip margins at the ends thereof, said sealing lips having a cross-section between said lip margins which is substantially wider than the corresponding cross-section of said lips at said lip margins to increase the closing bias of said lips.

2. A dental syringe safety sheath according to claim 1 wherein the material forming each of said lips generally thickens as said lips extend from said ends of said slit to the generally central portion of each of said lips.

3. A dental syringe safety sheath according to claim 1 wherein said sealing lips are defined in part by convex outer surfaces extending between said ends of said slit.

4. A dental syringe safety sheath according to claim 1 wherein said sealing lips have a substantially circular cross-section.

5. A dental syringe safety sheath according to claim 1 wherein the material defining said substantially wedge-shaped cavity has a substantially circular cross-section.

6. A dental syringe safety sheath according to claim 1 wherein the collective width of said lips measured along a discrete portion of said lips between said ends of said slit is at least as great as the length of said lips measured along said slit.

7. In a dental syringe safety sheath adapted to cover the nozzle of a dental syringe having an discharge orifice wherein the sheath includes a generally tubular resilient body member having a nozzle engaging portion configured to substantially fit over and cover said nozzle and a tapered discharge portion located downstream therefrom and wherein said tapered discharge portion includes a tapered external surface and an internal fluid passageway defining a one-way valve of duckbill type construction, the improvement comprising a pair of sealing lips with an outlet slit disposed therebetween and lip margins at the ends thereof, said sealing lips having a cross-section between said lip margins which is substantially wider than the corresponding cross-section of said lips at said lip margins to increase the closing bias of said lips.

8. A dental syringe safety sheath according to claim 7 wherein the material forming each of said lips generally thickens as said lips extend from said ends of said slit to the generally central portion of each of said lips.

9. A dental syringe safety sheath according to claim 7 wherein said sealing lips are defined in part by convex outer surfaces extending between said ends of said slit.

10. A dental syringe safety sheath according to claim 7 wherein said sealing lips have a substantially circular cross-section.

11. A dental syringe safety sheath according to claim 7 further comprising a substantially wedge-shaped cavity having a substantially circular cross-section.

12. A dental syringe safety sheath according to claim 7 wherein the collective width of said lips measured along a discrete portion of said lips between said ends of said slit is at least as great as the length of said lips measured along said slit.

* * * * *